United States Patent
Hannes et al.

(10) Patent No.: US 9,107,670 B2
(45) Date of Patent: Aug. 18, 2015

(54) IMPLANT, ESPECIALLY FOR THE OCCLUSION OF BIFURCATION ANEURYSMS

(75) Inventors: Ralf Hannes, Dortmund (DE); Hermann Monstadt, Bochum (DE)

(73) Assignee: Phenox GmbH, Bochum (DE)

( * ) Notice: Subject to any disclaimer, the term of this patent is extended or adjusted under 35 U.S.C. 154(b) by 0 days.

(21) Appl. No.: 14/000,658

(22) PCT Filed: Feb. 22, 2012

(86) PCT No.: PCT/EP2012/000772
§ 371 (c)(1),
(2), (4) Date: Oct. 28, 2013

(87) PCT Pub. No.: WO2012/113554
PCT Pub. Date: Aug. 30, 2012

(65) Prior Publication Data
US 2014/0058420 A1   Feb. 27, 2014

(30) Foreign Application Priority Data
Feb. 22, 2011   (DE) .......................... 10 2011 011 869

(51) Int. Cl.
*A61F 2/01* (2006.01)
*A61B 17/12* (2006.01)
*A61F 2/82* (2013.01)

(52) U.S. Cl.
CPC ..... *A61B 17/12113* (2013.01); *A61B 17/12022* (2013.01); *A61B 17/12118* (2013.01); *A61F 2/013* (2013.01); *A61F 2002/823* (2013.01)

(58) Field of Classification Search
CPC .............. A61F 2/01; A61F 2/06; A61F 2/013
USPC ................................. 623/1.35–1.48; 606/200
See application file for complete search history.

(56) References Cited

U.S. PATENT DOCUMENTS

| | | | | |
|---|---|---|---|---|
| 7,857,844 | B2 * | 12/2010 | Norton et al. ................ | 623/1.53 |
| 8,357,179 | B2 * | 1/2013 | Grandfield et al. ........... | 606/200 |
| 8,574,262 | B2 * | 11/2013 | Ferrera et al. ................. | 606/200 |
| 2006/0064151 | A1 * | 3/2006 | Guterman et al. ............. | 623/1.3 |
| 2007/0198075 | A1 * | 8/2007 | Levy ............................ | 623/1.11 |
| 2007/0203567 | A1 * | 8/2007 | Levy ............................ | 623/1.15 |
| 2007/0270902 | A1 * | 11/2007 | Slazas et al. .................. | 606/200 |
| 2008/0046072 | A1 * | 2/2008 | Laborde et al. ............... | 623/1.34 |
| 2008/0125855 | A1 * | 5/2008 | Henkes et al. ................ | 623/1.18 |
| 2010/0152834 | A1 | 6/2010 | Hannes et al. | |
| 2011/0160763 | A1 * | 6/2011 | Ferrera et al. ................. | 606/200 |

(Continued)

*Primary Examiner* — Suzette J Gherbi
(74) *Attorney, Agent, or Firm* — Berliner & Associates

(57) ABSTRACT

The invention relates to an implant (1) to be used for the occlusion of aneurysms in the region of vessel branches, in particular bifurcation aneurysms (A), with a mesh structure (3, 4), said implant comprising—from proximal to distal—sections (a) to (d) where (a) is a section tapering down proximally in which the mesh structure is brought together to form one or several coupling elements (10).

(b) is a fixing section by means of which the implant can be supported on the to wall of a vessel, (c) is a permeable section for the region of the vessel bifurcation, and (d) is a distal section in which the implant is expanded in comparison to section (b) and which is intended for placement into the aneurysm (A), wherein a separation zone (T1, T2) being arranged in the area of sections (c) or (d).

12 Claims, 10 Drawing Sheets

(56) References Cited

U.S. PATENT DOCUMENTS

| | | |
|---|---|---|
| 2011/0184451 A1 | 7/2011 | Sahl |
| 2011/0224707 A1 | 9/2011 | Miloslavski et al. |
| 2011/0319917 A1* | 12/2011 | Ferrera et al. ............... 606/159 |
| 2013/0138193 A1 | 5/2013 | Durand et al. |
| 2013/0211492 A1 | 8/2013 | Schneider et al. |
| 2013/0296916 A1 | 11/2013 | Monstadt et al. |
| 2014/0058498 A1 | 2/2014 | Hannes et al. |
| 2014/0343595 A1 | 11/2014 | Monstadt et al. |

\* cited by examiner

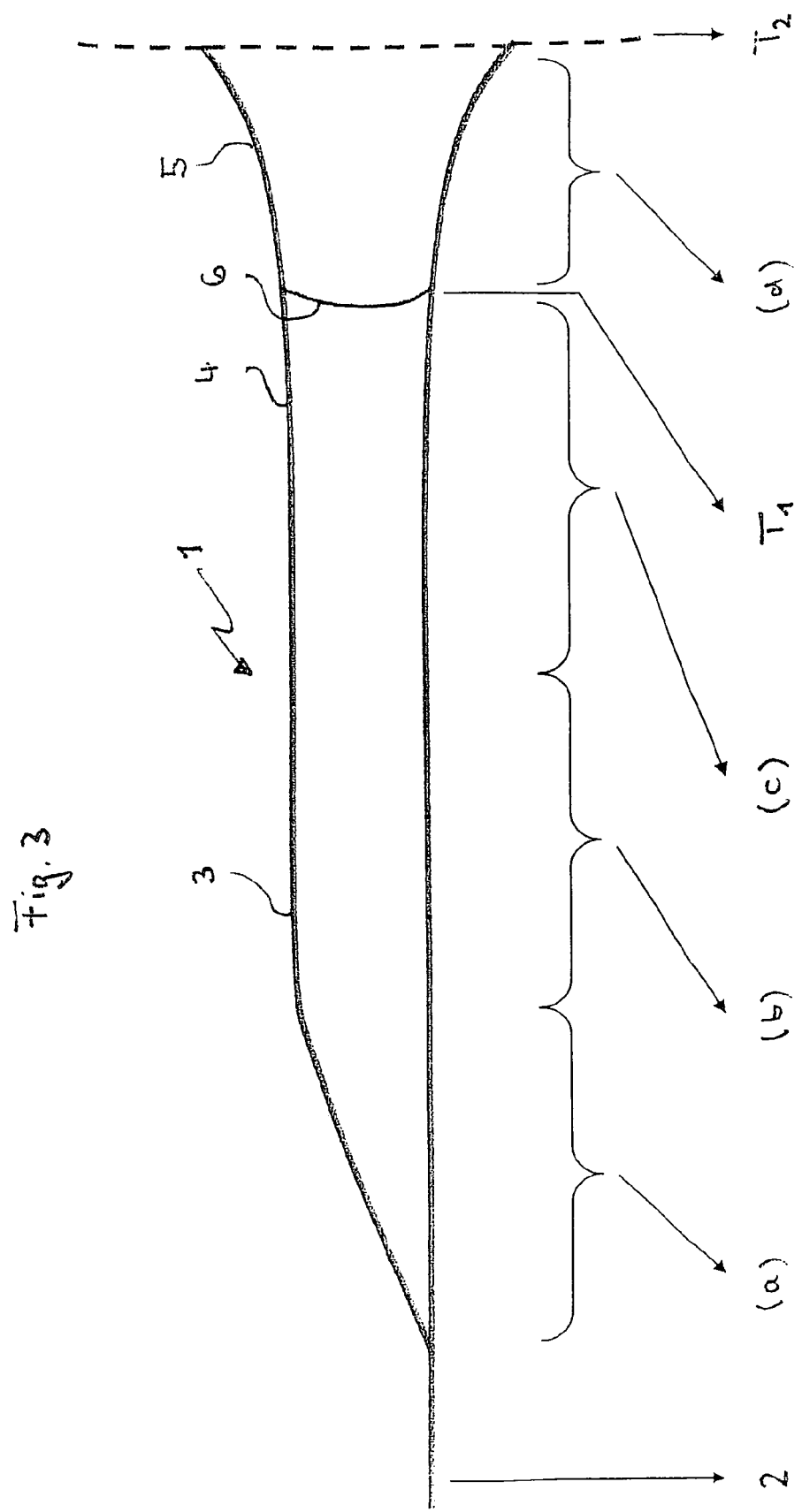

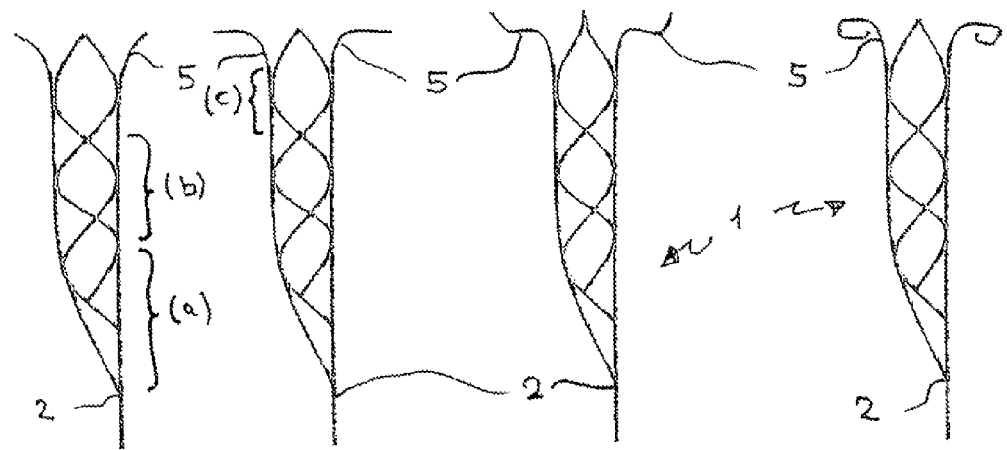
Fig. 5a      Fig. 5b      Fig. 5c      Fig. 5d
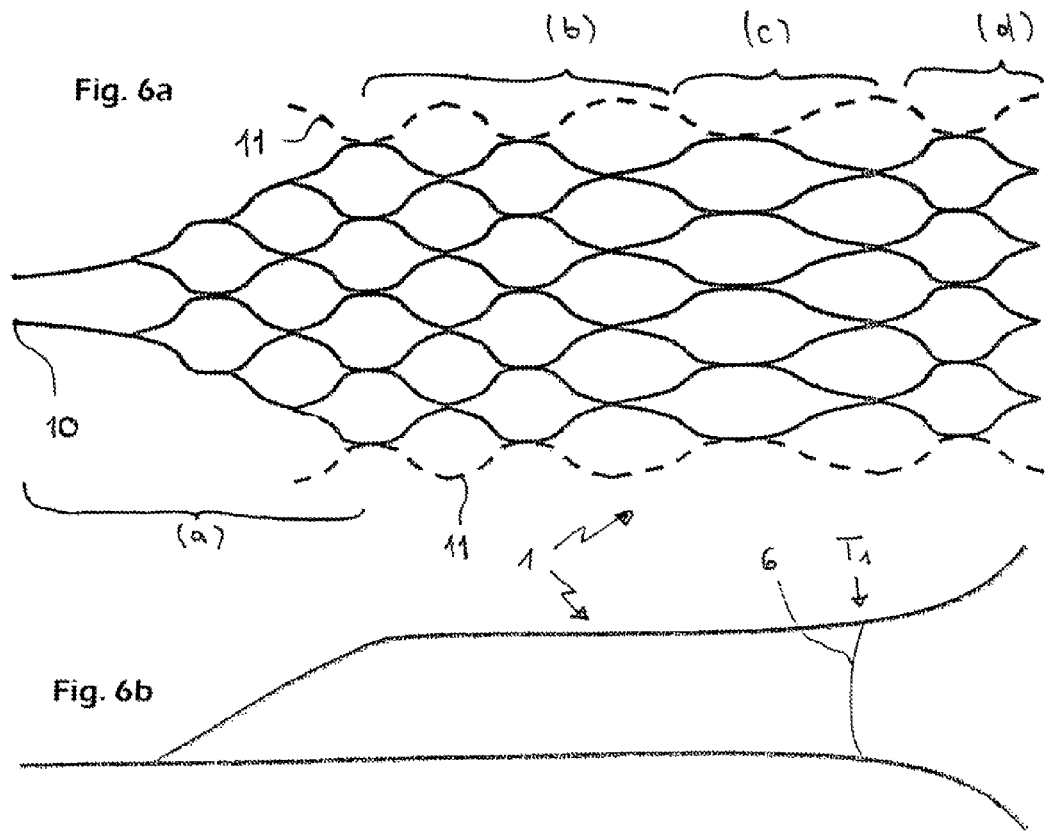

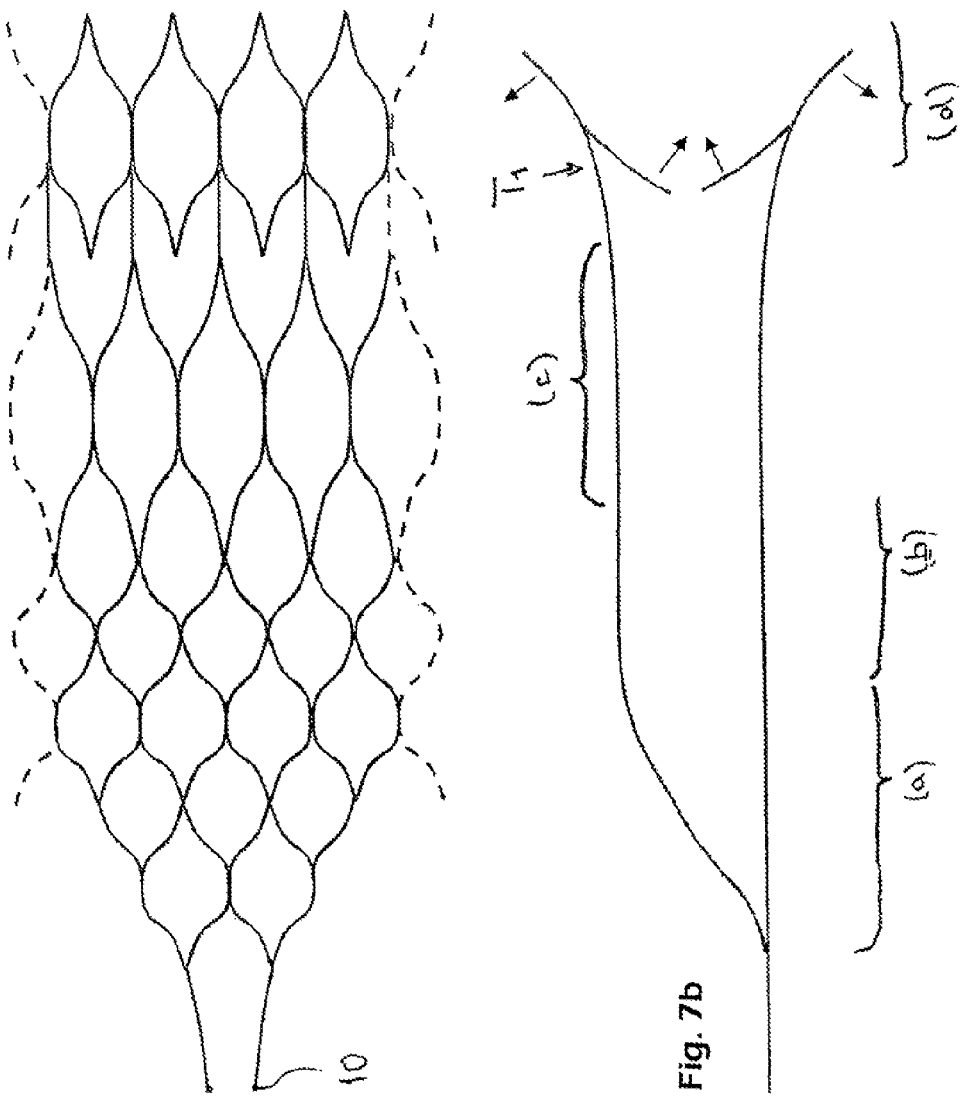

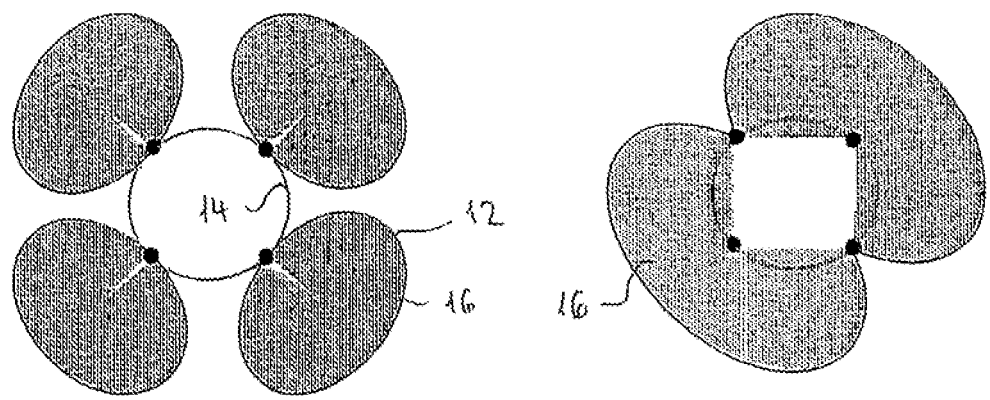
Fig. 8f                    Fig. 8g
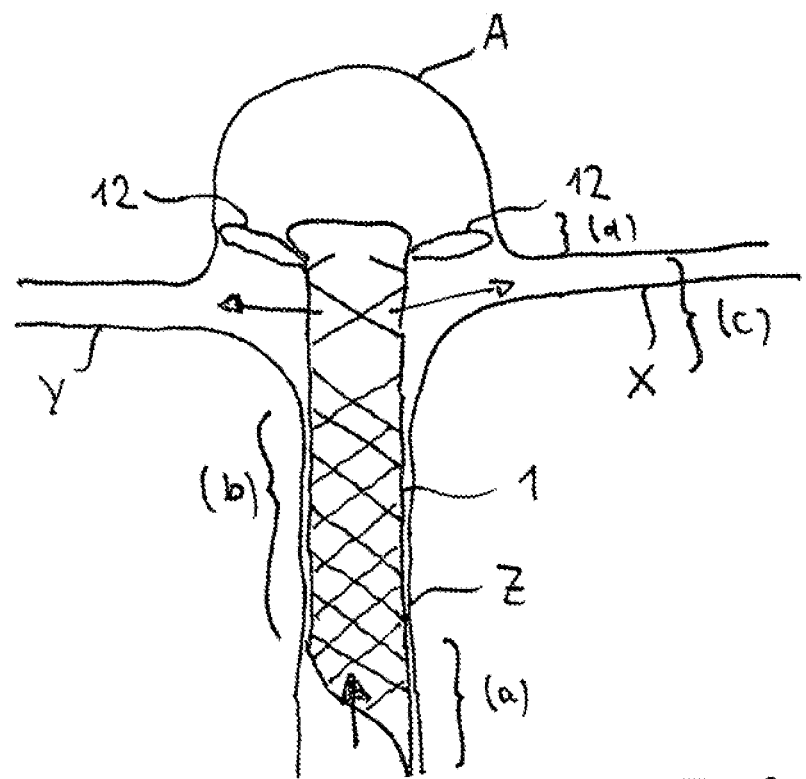
Fig. 9

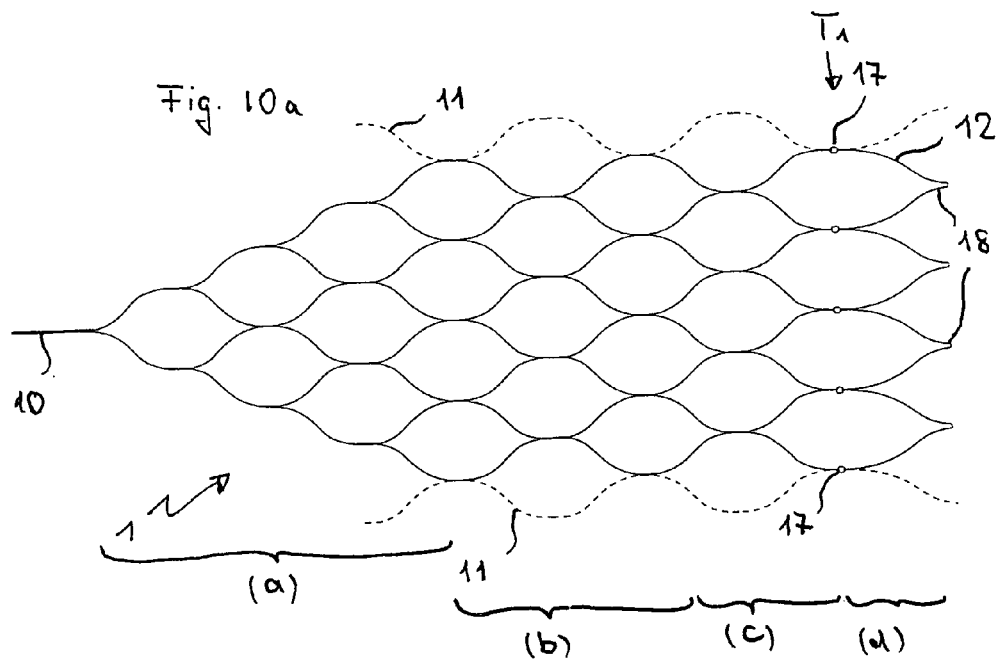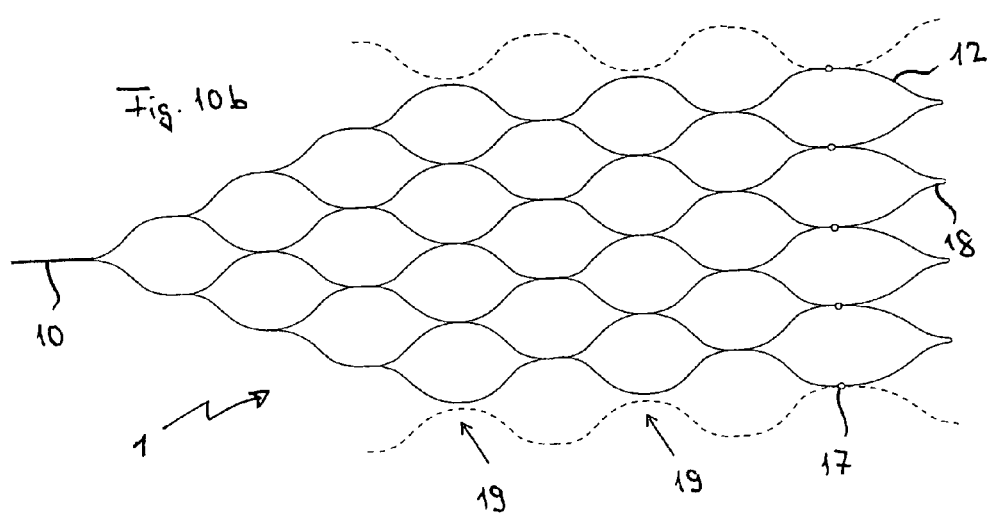

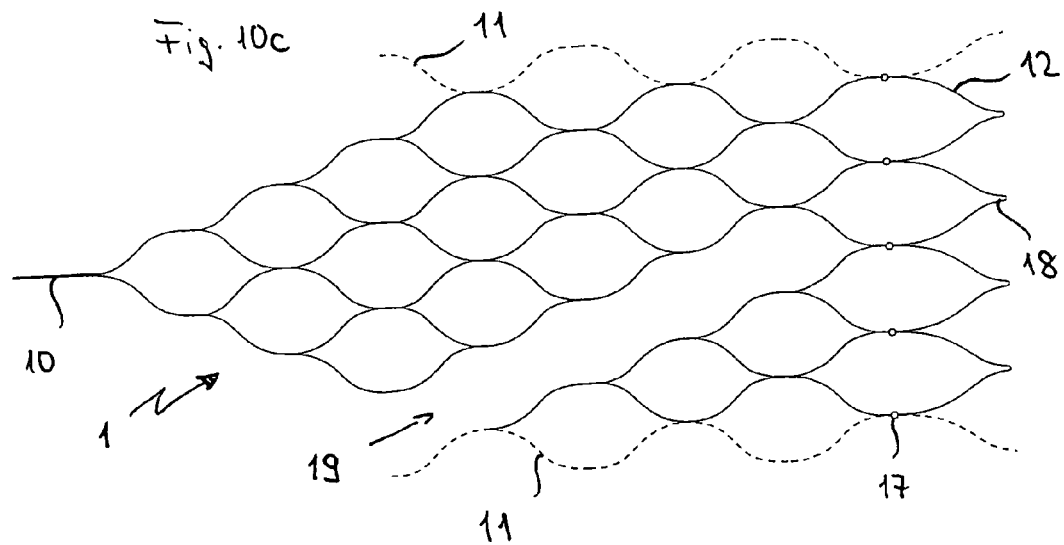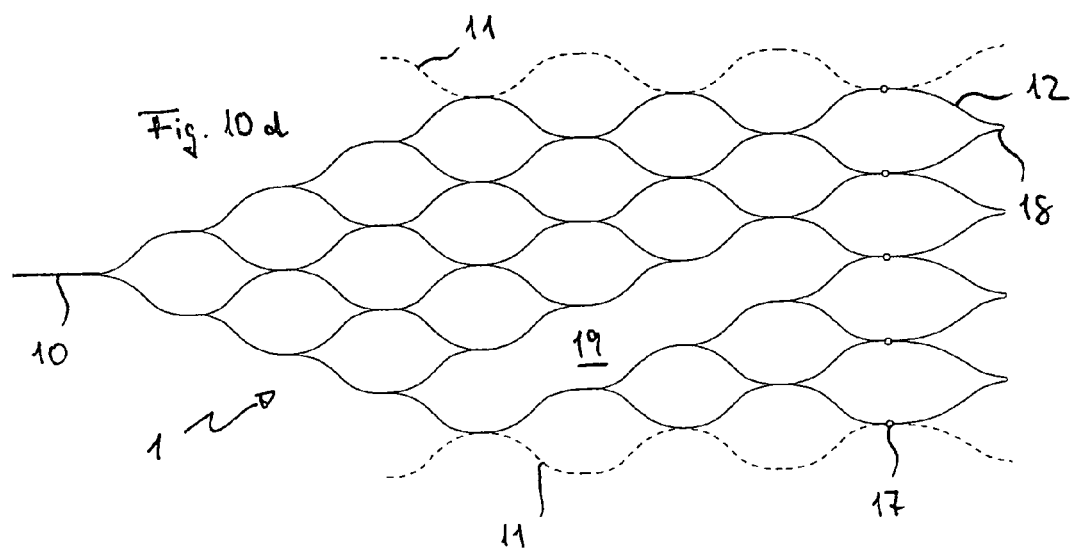

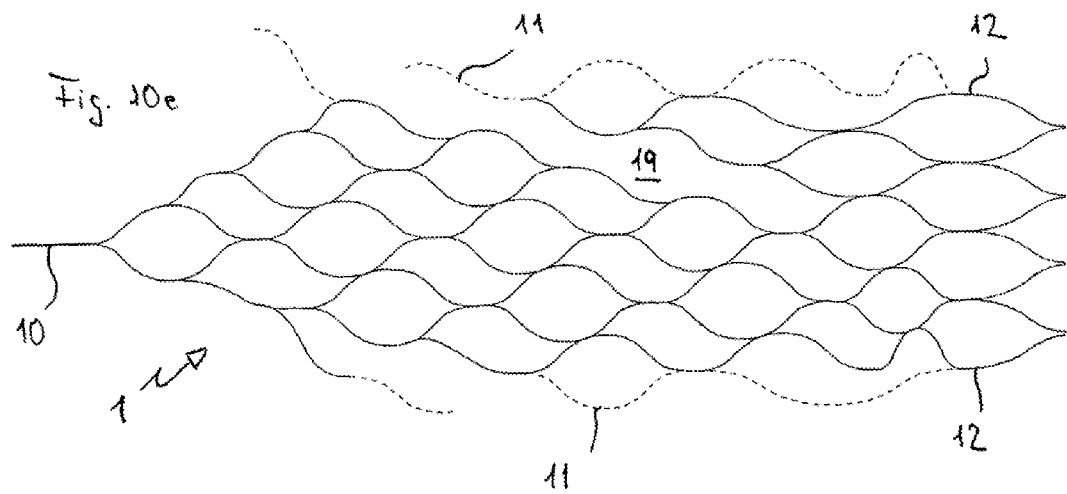
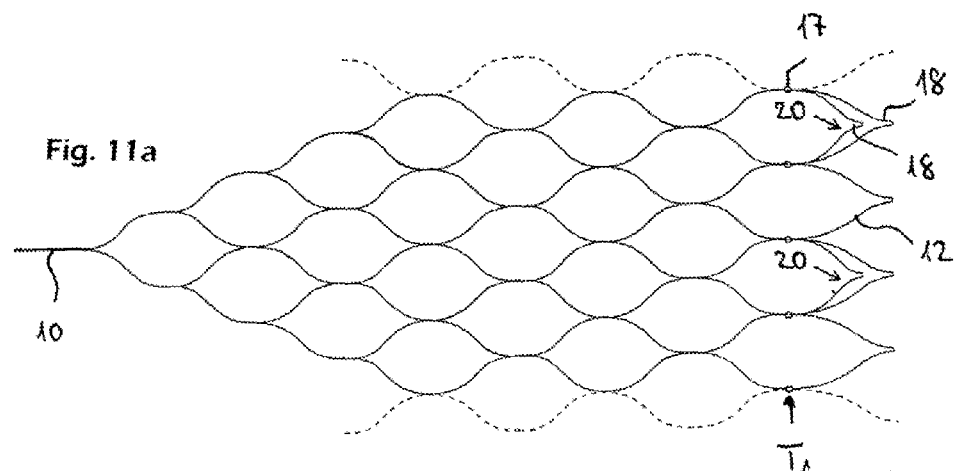
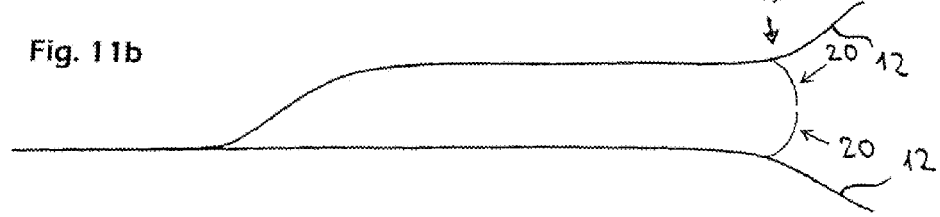

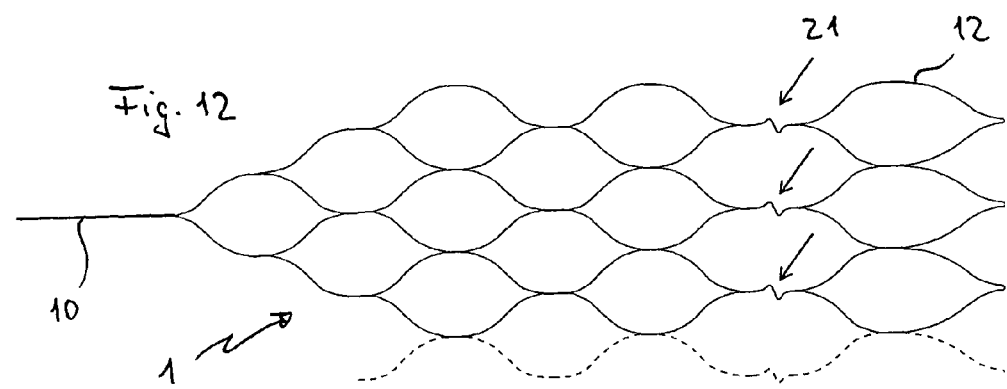
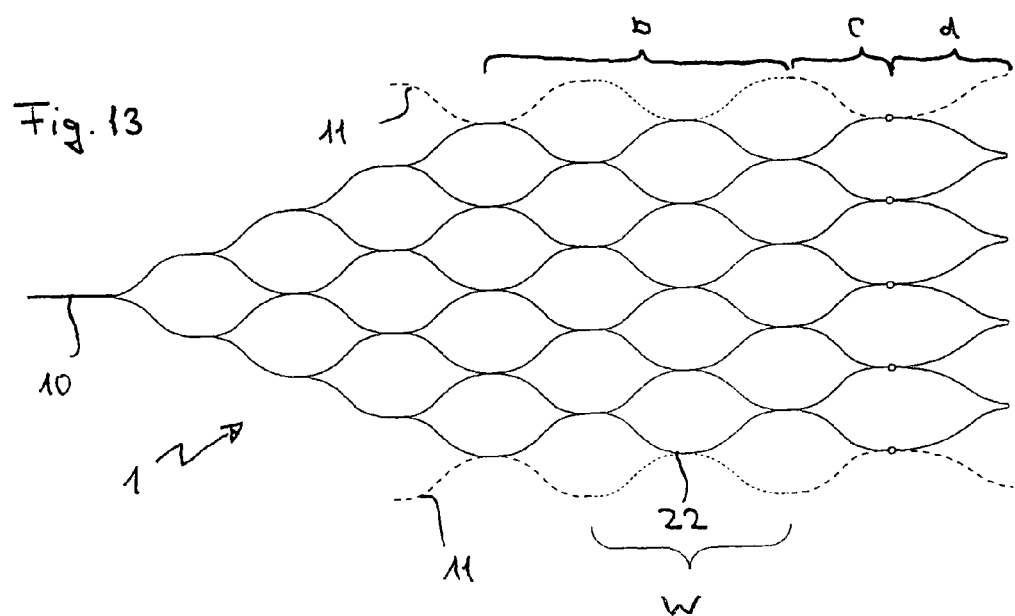

IMPLANT, ESPECIALLY FOR THE OCCLUSION OF BIFURCATION ANEURYSMS

The invention relates to an implant to be used for the occlusion of aneurysms in vessel branches, in particular bifurcation aneurysms. Using a catheter and guidewire such an implant is to be transported to the placement site for the purpose of implanting it permanently. Accordingly, the invention also relates to such an implant which is attached to a guidewire so as to be ready for implantation.

Arteriovenous malformation may significantly impair a patient and may even result in fatal risks. In particular, this applies to aneurysms, especially when these are found to exist in the cerebral region. Usually it is attempted to occlude malformations of this nature by means of implants. Such implants are as rule placed by endovascular methods using catheters.

Especially when treating cerebral aneurysms implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach only suits aneurysms that have a relatively narrow access to the vessel system, so-called aciniform aneurysms. In the event of blood vessel protuberances having a wide access to the blood vessel there is a risk that the implanted spirals or coils may be flushed out. These may then come to rest in other regions of the vascular system where they may cause further damage.

In such cases it has already been proposed to place into position a kind of stent that "bars" the opening of the aneurysm and in this way prevents the occlusion coils from being flushed out. Such stents are designed to have a relatively widemesh wall and have already been employed to treat some forms of aneurysms.

Vessel branches, in particular vessel bifurcations are a quite frequently occurring phenomenon. In case of a weak vessel wall the blood stream through an artery that acts on the front wall in a bifurcation quickly causes a protuberance or bulge which is prone to quickly dilate further. More often than not, such bifurcation aneurysms have a wide neck which prevents occlusion coils from being placed.

Moreover, stent structures are missing that are conducive to "barring" the entry opening to the aneurysm in the region of vessel branching. Such stents can only be manufactured with difficulty and at high costs; moreover, placement of such stents is extremely intricate as well, With this in mind, it is the objective of the present invention to provide an implant capable of being used especially in the region of bifurcation aneurysms where it serves to "bar" the access opening of an aneurysm. By means of occlusion coils subsequently introduced the aneurysm can then be closed off.

"Barring" the aneurysm in this way is also conceivable with a view to influencing the flow of blood to reduce the number of occlusion coils or even bring it down to zero.

This objective is achieved by providing an implant having a mesh structure, said implant comprising—from proximal to distal—sections (a) to (d) where (a) is a section tapering down proximally in which the mesh structure is brought together to form one or several coupling elements, (b) is a fixing section by means of which the implant can be supported on the wall of a vessel, (c) is a permeable section for the region of the vessel bifurcation, and (d) a distal section in which the implant is expanded in comparison to section (b) and which is intended for placement into the aneurysm, wherein a separation zone being arranged in the area of sections (c) or (d), in particular between sections (c) and (d).

The terms "proximal" and "distal" are to be understood such that they refer to parts of the implant that point towards the guidewire and thus towards the catheter and attending physician (proximal), or as the case may be to parts that point away from the guidewire or attending physician (distal). Accordingly, proximal refers to items facing the guidewire whereas distal means facing away from the guidewire.

The implant according to the invention is provided with a mesh structure which may consist of a braiding of individual wires, with a mesh structure cut from a tube or with a mesh structure being a combination of the two. In that regard, the implant is to be generally viewed as a stent or stent-like object distinguished by its specialized way of application and design.

The inventive implant is divided into four sections, i.e. sections (a) to (d), as viewed from proximal to distal.

Section (a) is a tapering proximal section which provides for the mesh structure to be brought together in the form of one or several coupling elements. Preferably, said coupling elements are located on the periphery, i.e. in implanted state they are situated at the vessel wall. For application related reasons a centered arrangement is not considered expedient; the peripheral location of the coupling element(s) enables the implant to be easier retracted into the placement catheter in the event of a misplacement. Embodiments provided with one or two coupling elements are preferred.

Section (b) serves for fixation and enables the implant to be supported on the wall of the vessel through which blood is led in. In this region the vessel is undamaged and its wall capable of accommodating a stent wall. In case of self-expanding implants section (b) is brought automatically in contact with the vessel wall when the stent has been released whereas implants placed in position and dilated by means of balloons are pressed against the vessel wall in this area via a placement balloon.

Section (c) is a permeable section which may in particular have a greater mesh size than section (b) and is arranged and placed in the zone where the vessel bifurcation is actually situated. A greater mesh size allows a more or less uninhibited flow of blood through the meshes into the efferent vessel branches.

In comparison to section (b) and usually also to section (c) the distal section (d) is of enlarged shape outwardly. It is to be placed into the aneurysm itself and shall adapt to the widened out wall of the aneurysm.

In the area of sections (c) and (d), in particular between sections (c) and (d) a separation zone is arranged which shall serve to retain occlusion means that have been arranged in the bifurcation aneurysm.

The enlargement of section (d) of the implant according to the invention preferably has a trumpet- or basket-like shape. Such an enlargement may also be created by providing a braiding or arranging loops. A loop-shaped enlargement of this kind usually comprises at least two loops, in particular three or more loops. Said loops may be made from appropriately formed wire elements but in the event the implant is cut from a tube may also be produced by adopting a laser cutting method to which said tube is then subjected.

The implants according to the invention may be manufactured from customary stent materials, for example of medical steel or cobalt-chromium alloys, however they consist in particular of shape-memory materials such as nitinol or ternary nickel-titanium alloys.

As mentioned hereinbefore, an implant according to the invention is preferably cut at least partially from a tube, in particular from a tube made of a shape-memory alloy.

The separation zone provided in the inventive implant extends in particular between sections (c) and (d). It is to be noted in this context that section (c) may be provided so as to assume an expanded shape at least within its distal end region as compared to section (b) which is helpful in the event the bifurcation aneurysm has already been formed in parts of the "impingement wall" of the vessel branch. In that case, the access portion of the aneurysm must be kept clear for the blood stream that branches off so that the separation zone extends within the aneurysm itself. The already enlarged portion of section (c) then merges into section (d), where it may expand further as the case may be. In this case as well the separation zone is arranged between sections (c) and (d). In case of a very shallow configuration of section (d) the separation zone may even coincide with section (d).

The separation zone on the one hand may be designed to comprise introduced fibers, threads, thin wires, a membrane or similar separation elements but may also be an integral part of the implant in the sense that the separation elements may be cut out of the basic tube and appropriately transformed for example in the shape of loops or webs. It is of prime importance that this separation zone performs its intended function which is to reliably retain occlusion means, for example occlusion coils, introduced into the distal area (d) of the implant or deflect the flow of blood in such a manner that further occlusion means are not needed.

If the separation zone is designed by introducing fibers, threads or thin wires it is considered expedient to arrange eyelets in the separation zone area. For example, the meshes of section (d) may be provided with relevant eyelets into which the nylon threads are knotted in a crosswise or starlike fashion.

However, the separation zone may also be created by means of curved elements cut from the tube material wherein the meshes of section (d) are deformed outwardly and the curved elements of the separation zone bent inwardly into the body of the implant. At least one curved element is required. If between two and four curved elements are applied these form a stable separation element which reliably retains the occlusion means introduced into an aneurysm.

The distal section (d) of the implant provided by the invention is designed so as to be particularly atraumatic, soft, and elastic. Walls of aneurysms are rather delicate and may rupture when forces are applied so this must by all means be prevented. To this end, especially the distal section (d) of the inventive implant has to be designed so as to be atraumatic. This is achieved by an arrangement of loops, for example, that adjust gently to the wall of the aneurysm in places where they are in contact. Same as in other regions of the implant such loops are produced by laser cutting from a tube, however, they may also be created by means of tacked on wires connected to section (c) by a laser welding method for example. This zone of transition coincides in particular with the separation zone but may as well constitute an extended area of section (c) with the separation zone being arranged distally of it.

It is of utmost importance here in the distal section (d) to join all wire ends in an atraumatic fashion to make sure aneurysm wall perforations cannot occur.

The meshes in the distal section (d) may terminate in rounded bends or arches, but especially at the distal end may also be provided in the form of nose-shaped rounded off and in this way atraumatically designed spouts. These rounded spouts enable the implant located in elongated shape inside the catheter to be easier moved with less force being needed for this.

The inventive implants may be provided in the form of a continuous laterally closed tube having a mesh structure but may also be slotted at the side either partially or all the way through. This slotted configuration may extend axially parallel or be of oblique/helical arrangement. In such a case, the mesh structure in the slotted areas is coiled up to suit the shape of the vessel, for example in the form of a rolled segment of a wire mesh fence. During placement such a slotted implant is capable of suitably adapting to the vessel lumen, especially of the supplying vessel, with a slight underlap (gap) or overlap of the lateral edges of the mesh structure being usually viewed to be unproblematic.

A partial slot terminating at the distal section (d) is preferred. By providing such a slotted arrangement the adjustment to the vessel configuration is enhanced, in particular in the area of sections (a) to (c), and the fixation of the implant inside the vessel improved. Surprisingly, it has been found that a slotted arrangement should not exert a negative influence on the radial force.

As a rule, the implants according to the invention are provided with marker elements facilitating their arrangement at the placement site. Marker element of this type are, for example, arranged in the area of the distal end of section (d), and may shape the connection points of joined wires so as to be atraumatic. However, such marker elements may also be provided in the form of windings at the wire loops or in the form of sleeves in the transition area of sections (c) and (d). For said marker elements in particular platinum and platinum alloy materials are suitable, for example alloys of platinum and iridium, as they are frequently used in prior art for marking purposes and as material for occlusion coils.

Moreover, the invention relates to an implant in accordance with the description hereinbefore, said implant being coupled to a customary guidewire. Such an attachment may, for example, be brought about by means of connection elements dissolving electrolytically under the influence of electric current. Such connection elements and materials have often been described in particular for the severance of occlusion coils and stents. Also a mechanical detachment through coupling elements may be realized without difficulty, with such coupling elements appropriately interacting with suitably designed coupling parts of the guidewire. Under the external restraint of a catheter or enclosure this connection remains intact; however, after the implant and its coupling location have been released from the catheter or enclosure the attachment disconnects causing the implant to be liberated together with the coupling elements forming part of the implant.

The inventive implants are placed with the help of a customary catheter or microcatheter; this is a proven technique which is frequently adopted.

The invention is explained in more detail by way of the enclosed figures where

FIG. 3 is a schematic diagram of the inventive implant with its sections;

FIG. 5 shows variants of section (d) of an implant according to the invention;

FIG. 6 depicts a preferred embodiment of an inventive implant as a spread planar representation;

FIG. 7 shows another embodiment of an inventive implant in accordance with FIG. 6;

FIG. 9 is the illustration of a bifurcation aneurysm with lateral vessels branching off the aneurysm area with an inventive implant in place;

FIG. 10 is a spread planar representation of variants of implants according to the invention;

FIG. 11 shows another variant with inwardly and outwardly oriented curved elements in section (d);

FIG. 12 shows another variant with articulated connectors in section (c); and

FIG. 13 illustrates another variant of an inventive implant having increased flexibility.

FIG. 1 shows a bifurcation aneurysm with a supplying vessel Z, two efferent vessels X and Y as well as the aneurysm A located within the bifurcation. The long arrows signify the flow of blood into the aneurysm A where it impinges on the aneurysm wall thus causing outward pressure and the aneurysm to enlarge (small arrows).

Figure 1:
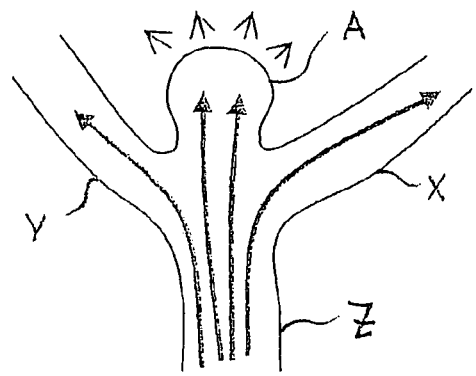
FIG. 1 is a schematic representation of a bifurcation aneurysm.
Figure 2:
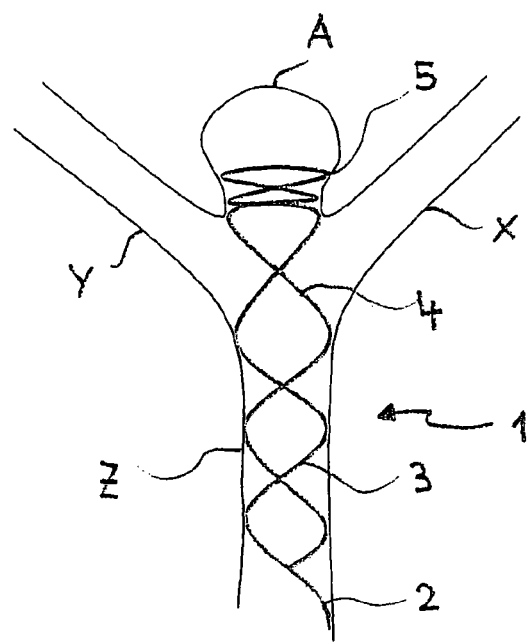
FIG. 2 shows schematically an inventive implant placed in the area of a vessel bifurcation with bifurcation aneurysm.

FIG. 2 shows a vessel configuration with an aneurysm A as described in FIG. 1 with an inventive implant 1 being arranged inside the aneurysm. The implant has a proximal end 2 which is provided with the coupling element and, before detachment, connected to the guidewire (not shown here). By way of its meshes 3 the implant 1 is anchored to the wall of the supplying vessel Z and in the region of the bifurcation has meshes 4 the mesh size of which is greater. A distal region 5 is shown in the neck of the aneurysm. Between the distal region 5 and the area where greater meshes 4 are located there is a separation zone intended to retain occlusion means introduced into the aneurysm A after the implant has been placed in position.

The enlarged meshes 4 in the area of the bifurcation enable the blood stream inflowing through the supplying vessel Z to be discharged without undue interference via branches X and Y. After the placement of occlusion means which are not illustrated here in the aneurysm A the flow of blood into aneurysm A is impeded to such an extent that a plug forms inside resulting in blocking off the aneurysm. Alternatively and provided the separation zone is sufficiently impermeable, an occlusion can be achieved without the use of occlusion means.

FIG. 3 is a schematic representation of an inventive implant showing its individual sections.

Implant 1 has a proximal section (a) in which the implant tapers off and terminates in a coupling element, shown here in the form of a wire. This sections corresponds to area 2 in FIG. 2.

Distally adjacent to it follows section (b) which serves to secure the implant at the wall of the supplying vessel Z. In this area the size of meshes 3 is relatively narrow so that positive contact with the vessel wall is achieved.

Also in distal direction follows section (c) where meshes 4 are arranged that have a relatively large mesh size. This area is intended to discharge inflowing blood into branches X and Y, see FIGS. 1 and 2 in this respect.

The distal end of the implant 1 is section (d) in which structure 5 in the illustrated case enlarges in a trumpet-like manner. This area will be located within aneurysm A. Section (d) may be an integral part of the implant, i.e. together with sections (a) to (c) be cut out of a tube (of nitinol) or formed into a braiding using wires of this material. However, it is also possible to cut sections (a) to (c) out of a tube, provide a braiding for section (d) and attach said braiding to section (c) by welding.

Separation zone T1 is arranged between sections (c) and (d), said separation zone consisting of one or several separation elements 6. These separation elements may be provided in the form of restrained threads, wires or fibers, for example of polyamide, but may as well consist of parts of a cut structure formed to have an inward orientation. Separation zone T1 with separation elements 6 serves to retain the occlusion means introduced into an aneurysm.

Depending on the nature of the aneurysm the separation zone may also be displaced into the section (d) or even be located at the distal end of the section (d). Such a separation zone T2 is especially useful if the bifurcation has been formed in such a way that the efferent vessels X and Y do not directly branch off from the supplying vessel Z but instead branch out of the aneurysm. In that case, the separation zone must be located directly above the branches in the dilating section of the implant. Section (d) is limited to the distal end of the implant 1 and extends into separation zone T2.

Figure 4:
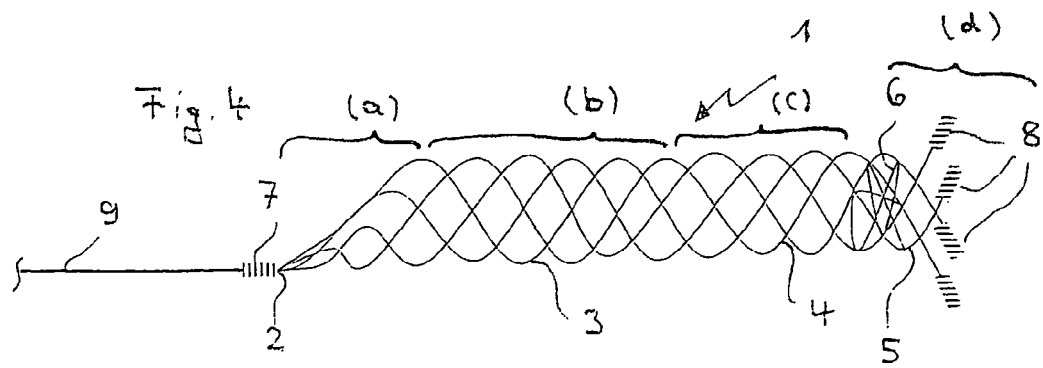
FIG. 4 illustrates an inventive implant as it can be employed as per FIG. 2.
Figure 8B:
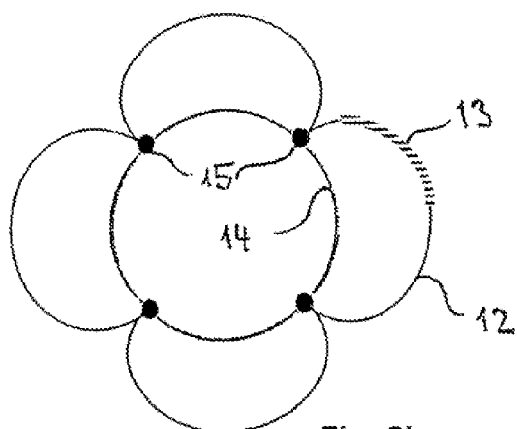
FIG. 8 shows variants of an implant according to the invention with loop-shaped distal sections (d)
Figure 8C:
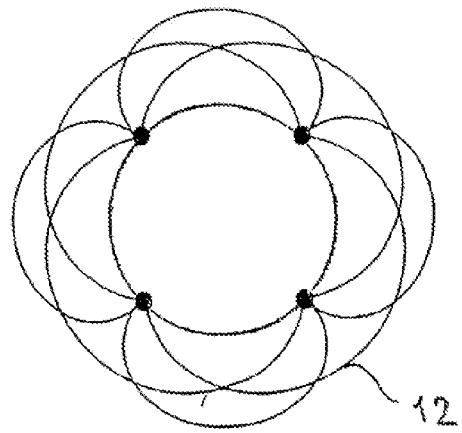
Figure 8A:
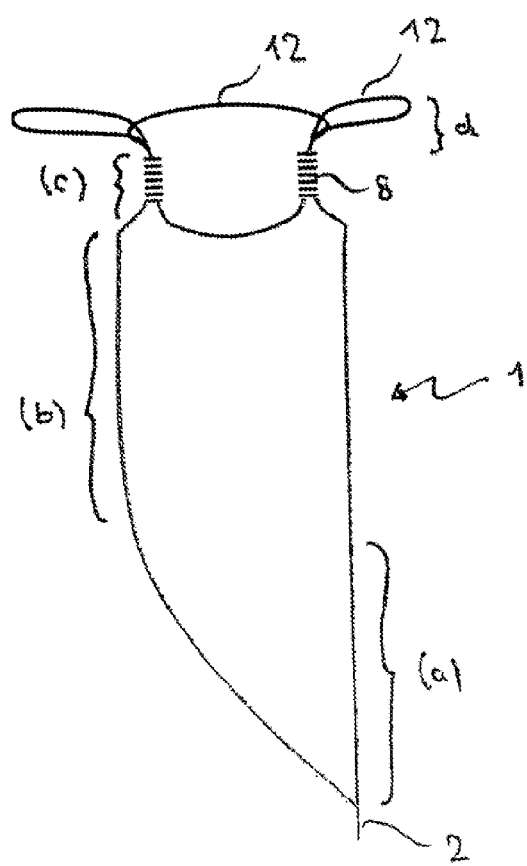
Figure 8D:
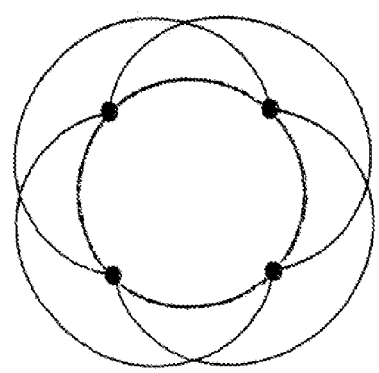
Figure 8E:
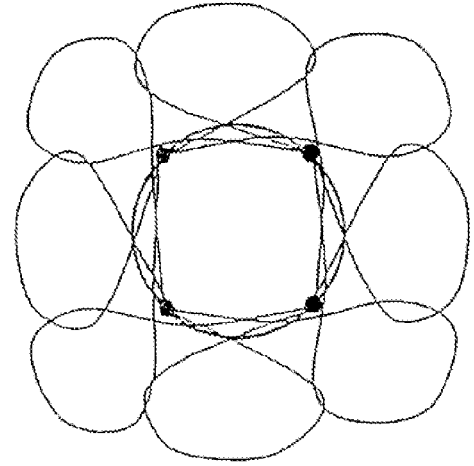

FIG. 4 illustrates an inventive implant 1 as it can be employed as per FIG. 2. The implant 1 is shown to include a guidewire 9 and has been provided with a radiopaque marker coil 7 arranged at its proximal end 2. The coupling element or elements connected to the implant 1 via the guidewire 9 are not shown in the illustration but are arranged in the region of marker coil 7.

The implant shown in the figure is a braiding of individual wires which are preferably made of nitinol and onto which the ultimate form of the implant has been impressed. Nitinol as shape-memory material enables the implant to be inserted into the catheter in compressed form without the shaping of the implant being lost. Having been liberated from the catheter the implant assumes the shape impressed on it so that it can fulfill its purpose as intended.

The implant 1 is divided into four sections (a) to (d), wherein section (a) is the tapering proximal section brought together at the proximal end 2 and terminating in one or several coupling elements. Section (b) has a fixation function and is in contact with the wall of the supplying vessel Z, said section is provided with relatively narrow meshes 3. The section (c) is designed so as to be permeable and provided with wider meshes 4 through which the flow of blood is allowed to be discharged into efferent vessels X and Y. In comparison with section (b) and also with respect to section (c) the section (d) is of enlarged shape and situated within the aneurysm A. The ends of the individual wires are designed so as to be atraumatic by providing marker coils 8 of a radiopaque material, for example platinum or a platinum alloy. Between sections (c) and (d) a fiber braiding 6 is to arranged which may consist of nylon for example and which also forms the separation zone T1. Reference numeral 5 signifies the meshes or filaments of the implant 1 that expand outwardly in the distal region.

FIG. 5 is a schematic drawing showing four variants of how the distal region 5 of implants 1 according to the invention can be designed. FIG. 5a shows a distal end of the implant that flares out in a trumpet-like form, i.e. section (d) is designed to form a chalice-shaped enlargement. As illustrated in FIG. 5b the distal end 5 has a disk-like enlargement with distal section (d) being extremely limited. FIG. 5c shows a combination of the design elements included in FIGS. 5a and 5b.

FIG. 5d illustrates a distal region where the distal ends of the individual filaments of an implant 1 are rolled up. For better orientation, sections (a), (b), (c) are also referred to in FIG. 5a resp. 5b.

FIG. 6 is the spread planar representation of a preferred embodiment of an inventive implant 1 showing sections (a) to (d). Implant 1 is to be understood as a mesh structure cut out of nitinol tube, wherein the webs 11 shown in the representation as a broken line correspond with the solid-line webs located on the opposite side. The larger honeycombs in the area of section (c) can be easily seen in the representation of FIG. 6a as well as the chalice- or trumpet-shaped enlargement shown in the schematic drawing as per FIG. 6b. Also illustrated there is separation zone T1 with separation elements in the form of an inserted level consisting of nylon threads 6.

FIG. 7 shows another embodiment of an inventive implant 1 which is cut out of nitinol tubing, said implant consisting of the proximally arranged coupling elements 10, the section (a) tapering off in proximal direction, a fixation section (b), a section of greater mesh size (c), and the widening out section (d). In this case as well and as has been shown in FIG. 6 a planar representation has been selected for the implant, wherein the implant has a special separation zone T1 comprising elements cut out of the nitinol tube, said elements are formed such that they fold inwardly while the distal end flares out outwardly assuming a trumpet-like shape. Same as the inserted nylon threads of the variant described by way of FIG. 6 the inwardly folding webs 6 of the separation zone T1 serve to retain the occlusion means introduced into an aneurysm.

The implants as per FIGS. 6 and 7 must not necessarily have a tubular structure but may also be provided in the form of rolled up "mats" that are braced in position against the wall of the vessel. The implants may also be partially slotted.

FIG. 8 depicts an inventive implant 1 in which the section (d) has a more disk-like shape, said section consisting for the main part of wire loops 12. Said wire loops connect to the cylindrical part of the implant body 1, with this cylindrical portion being composed of the sections (a) to (c). In the transitional area adjacent to the attached loops 12 marker elements 8 are arranged which shall ensure the implant is safely placed. In the region where the cylindrical body of the implant 1 connects to section (d) in which loops 12 are located there is the section (c) which enables the discharge of the inflowing blood through the laterally efferent vessels. The blood thus enters the efferent vessels (X and Y, FIG. 2) between the webs provided with marker elements 8.

Individual variants of the distal section (d) are shown in FIGS. 8b to 8g as a top view representation, wherein individual or several loops 12 can be provided with marker coils 13. The marker coils 13 may embrace the loops either wholly or in part. In the case shown in the figure the loops originate from four connectors 15 that also carry the marker elements 8, with the inner circle 14 constituting the transition to the cylindrical portion of the implant as can be seen from representations 8b to 8g. Any bracings that may exist for a separation zone T1 or T2 are not shown.

The embodiments illustrated in FIGS. 8f and g show loops 12 that are provided with an extensible membrane 16, said loops simultaneously functioning as a separation zone T2, as depicted in FIG. 3.

It is to be understood that separation zones T1 and T2 must partition off the section of aneurysm A that has to be occluded. Depending on the type of aneurysm this separation zone may be situated in the entry region—in the case of vessels branching off proximally to the entry region—or within the aneurysm—in the to case two vessels branch off out of the aneurysm space itself—while in the latter case only that portion of the aneurysm can be occluded that is free from branching off vessels. Especially in the event of disk-shaped distal sections (d) of the inventive implants an additional bracing or arrangement of separation elements cut out of the tube may be dispensed with, particularly when a greater number of wire loops have been provided.

Same as the remaining body of the implant the loop-shaped distal sections (d) illustrated in FIG. 8 may, on the one hand, be cut out of a tube of suitable diameter. However, it is also possible to cut sections (a) to (c) of the implant body from a tube in a customary manner and attach to it section (d) consisting of wire filaments, for example by means of a laser welding method.

FIG. 9 shows a special case of an aneurysm A with efferent vessels X and Y branching off out of the aneurysm. In this instance, the implants 1 described by way of FIG. 8 are particularly useful, said implants having loops 12 simultaneously forming the separation zone T2 and, inside the aneurysm itself, being located distally of the branching off vessels. The cylindrical body of the implant 1 with sections (a) and (b) is located within the supplying vessel Z, the section (c) allowing blood to pass through into the branches X and Y is situated in the area of these branches, and section (d) with loops 12 is arranged distally adjacent to said section (c). The loops may be covered by a membrane, with said membrane consisting of an extensible material, for example teflon, or a non-woven fabric. Such a non-woven fabric of polycarbonate urethane is known from publication DE 28 06 030 and is characterized by high elasticity conducive to the placement of the implant through a catheter. The membrane may be of slotted, folded or porous design, for instance to save material and facilitate transportation via a catheter.

Such a membrane may also be used as separation element for the separation zone arranged between the sections (c) and (d).

FIG. 10 is a spread out planar representation of several preferred embodiments of an implant 1 according to the invention, wherein the honeycomb structure is composed of honeycombs of substantially equal size, with the exception of the distal loops where the honeycomb surface is larger.

Same as depicted in FIG. 6 the webs 11 shown as a broken line coincide with the solid-line webs on the opposite side. Accordingly, the implant 1 corresponds to a tube having a lattice or honeycomb structure.

Attached to the proximally arranged coupling element 10 follows the proximal section (a) which in turn is followed by the fixation section (b). The distal section (d) starts in the region of eyelets 17 which serve to accommodate and secure wire or nylon elements by means of which a separation level is arranged within the implant. The distal loops located within the outwardly flared section (d) are distally provided with rounded spouts which are conducive to the positioning of the implant at the placement site via a catheter.

FIG. 10b corresponds in all significant aspects with the representation of FIG. 10a with the exception that a partial slotting is provided in the region of arrows 19, i.e. the location where the tubular structure of the implant 1 is not closed. The slotted configuration extends axially parallel and ends ahead of the distal section (d) at a point where the permeable section (c) is located.

FIG. 10c shows a variant in which a slot 19 is arranged that does not have an axially parallel extension and coils up around the longitudinal axis; however, it also ends ahead of distal section (d).

Slotted arrangements of this nature have proved to be of considerable advantage in terms of flexibility in the area of the fixation zone (b). The radial force of the implant 1 is not significantly impaired in this way but adaptation to the vessel configuration and vessel lumen is improved.

FIG. 10d also shows an inventive implant provided with slots, in this case, however, the slotting does not extend up to the edges of the implant.

Another variant provided with slot 19 is illustrated in FIG. 10e, said slot also coiling up around the longitudinal axis but with honeycomb forms existing side by side. The form of the honeycombs has an effect on the flexibility and can be selected so as to satisfy the relevant needs.

In FIG. 10 all the loops, resp. honeycombs of the distal section (d) are identified by means of reference numeral 12.

FIG. 11 depicts another variant of an inventive implant 1 provided with an individual coupling element 10 and a substantially regular honeycomb structure, wherein additional loops 20 are arranged as separation elements. In this respect the embodiment shown in FIG. 11 corresponds with the embodiment in FIG. 7. In the implanted product the additional loops 20 are pointing to the inside and constitute separation level T1. These loops 20 are also provided with rounded spouts 18 intended to facilitate transportation through a catheter.

FIG. 11b is a schematic representation of the implant shown in FIG. 11a with inwardly pointing loops 20 and the separation level T1.

FIG. 12 shows another variant of a particularly flexible implant 1 with articulated connectors 21 in the form of a zigzag arrangement of the respective webs provided with a view to improving the adaptation of the implant 1 to curved vessel configurations in the region of the bifurcation.

Finally, FIG. 13 shows another variant including in section (b) a number of honeycombs having thinner webs (region W) to increase both flexibility and bendability. This area 22 is situated in the fixation zone (b) and intended to meet requirements associated with an irregular vessel configuration in the fixation zone. Otherwise, the implant 1 corresponds with the above described variants.

The invention claimed is:

1. Implant (1) to be used for the occlusion of bifurcation aneurysms (A), with a mesh structure (3, 4), said implant comprising—from proximal to distal—sections (a) to (d):
    (a) is a section tapering down proximally in which the mesh structure is brought together to form one or several coupling elements (10),
    (b) is a fixing section by means of which the implant can be supported on the wall of a vessel,
    (c) is a permeable section for a region of vessel bifurcation, and
    (d) is a distal section in which the implant is expanded in comparison to section (b) and which is intended for placement into the aneurysm (A),
    wherein a separation zone (T1) is arranged in between sections (c) and (d), the separation zone (T1) being provided with separation elements consisting of filaments (6) extending substantially in a plane crosswise to the implant (1), and the distal section (d) consisting of a plurality of loops (12).

2. Implant according to claim 1, characterized in that the distal section (d) is widened out in a trumpet- or basket-like shape through a braiding or by means of the loops (12).

3. Implant according to claim 1, characterized in that it consists of shape-memory material.

4. Implant according to claim 1, characterized in that the implant at least partially is cut out of a tube.

5. Implant according to claim 1, characterized in that the proximal section (a) terminates in a coupling wire (10).

6. Implant according to claim 1, characterized in that the distal section (d) is designed so as to be atraumatic, soft, and elastic.

7. Implant according to claim 1, characterized in that the loops (12) are provided with eyelets (17) in the distal section (d).

8. Implant according to claim 1, characterized in that the loops (12) in the distal section (d) are provided at the distal end with rounded spouts (18).

9. Implant according claim 1, characterized in that it is of laterally closed tubular design.

10. Implant according to claim 1, characterized in that the implant is partially or continuously slotted.

11. Implant according to claim 1, characterized in that marker elements (8) are arranged in the distal section (d).

12. Implant according to claim 1 which is coupled to a guidewire (9).

* * * * *